(12) United States Patent
Friedman et al.

(10) Patent No.: US 6,645,162 B2
(45) Date of Patent: *Nov. 11, 2003

(54) SYSTEMS AND METHODS FOR ULTRASOUND ASSISTED LIPOLYSIS

(75) Inventors: Zvi Friedman, Qiriat Bialik (IL); Dov Maor, Haifa (IL); Shuki Vitek, Haifa (IL)

(73) Assignee: Insightec - Txsonics Ltd., Tirat Carmel (IL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 2 days.

This patent is subject to a terminal disclaimer.

(21) Appl. No.: 09/879,262

(22) Filed: Jun. 11, 2001

(65) Prior Publication Data

US 2002/0082589 A1 Jun. 27, 2002

Related U.S. Application Data

(63) Continuation-in-part of application No. 09/753,273, filed on Dec. 27, 2000.

(51) Int. Cl.[7] ................................................. A61N 7/00
(52) U.S. Cl. ............................................ 601/2; 604/22
(58) Field of Search ................................ 601/2; 604/22

(56) References Cited

U.S. PATENT DOCUMENTS

| 4,886,491 A | 12/1989 | Parisi et al. |
| 4,888,746 A | 12/1989 | Wurster et al. |
| 5,015,929 A | * 5/1991 | Cathignol et al. .......... 310/334 |
| 5,143,063 A | * 9/1992 | Fellner ....................... 128/897 |
| 5,209,221 A | 5/1993 | Riedlinger |
| 5,291,890 A | 3/1994 | Cline et al. |

(List continued on next page.)

FOREIGN PATENT DOCUMENTS

| EP | 0 734 742 A2 | 10/1996 |
| WO | WO 91/15999 | 10/1991 |

OTHER PUBLICATIONS

Glossary 70 words, Lipoinfo.com, pp. 1–14, Mar. 17, 2000, http://www.lipoinfo.com/glossary.htm.

(List continued on next page.)

*Primary Examiner*—Linda C. M. Dvorak
*Assistant Examiner*—Henry M. Johnson
(74) *Attorney, Agent, or Firm*—Bingham McCutchen LLP

(57) ABSTRACT

Cells are destroyed within a subcutaneous tissue region using a transducer disposed externally adjacent to a patient's skin. The transducer emits acoustic energy that is focused at a linear focal zone within the tissue region, the acoustic energy having sufficient intensity to rupture cells within the focal zone while minimizing heating. The transducer may include one or more transducer elements having a partial cylindrical shape, a single planar transducer element coupled to an acoustic lens, or a plurality of linear transducer elements disposed adjacent one another in an arcuate or planar configuration. The transducer may include detectors for sensing cavitation occurring with the focal zone, which is correlated to the extent of cell destruction. A frame may be provided for controlling movement of the transducer along the patient's skin, e.g., in response to the extent of cell destruction caused by the transducer.

31 Claims, 7 Drawing Sheets

U.S. PATENT DOCUMENTS

| | | | | |
|---|---|---|---|---|
| 5,419,761 A | | 5/1995 | Narayanan et al. | |
| 5,507,790 A | * | 4/1996 | Weiss | 128/897 |
| 5,514,086 A | | 5/1996 | Parisi et al. | |
| 5,527,273 A | | 6/1996 | Manna et al. | |
| 5,601,526 A | * | 2/1997 | Chapelon et al. | 601/2 |
| 5,725,482 A | | 3/1998 | Bishop | |
| 5,743,863 A | * | 4/1998 | Chapelon | 601/2 |
| 5,769,879 A | | 6/1998 | Richards et al. | |
| 5,823,990 A | | 10/1998 | Henley | |
| 5,827,204 A | * | 10/1998 | Grandia et al. | 601/2 |
| 5,884,631 A | | 3/1999 | Silberg | |
| 5,938,608 A | | 8/1999 | Bieger et al. | |
| 6,013,048 A | | 1/2000 | Podany et al. | 604/22 |
| 6,032,675 A | * | 3/2000 | Rubinsky | 128/898 |
| 6,033,375 A | | 3/2000 | Brumbach | |
| 6,036,644 A | | 3/2000 | Schutt | |
| 6,039,048 A | | 3/2000 | Silberg | |
| 6,045,777 A | | 4/2000 | Church et al. | |
| 6,071,239 A | * | 6/2000 | Cribbs et al. | 600/439 |
| 6,106,511 A | * | 8/2000 | Jensen | 600/102 |
| 6,113,559 A | * | 9/2000 | Klopotek | 601/3 |
| 6,135,971 A | * | 10/2000 | Hutchinson et al. | 601/3 |
| 6,156,549 A | * | 12/2000 | Drewes et al. | 435/173.7 |
| 6,350,245 B1 | * | 2/2002 | Cimino | 601/2 |

OTHER PUBLICATIONS

"External Ultrasonic Liposuction", Mar. 17, 2000, http://www.lipoinfo.com/chap14..htm.

Bates, B., "External Ultrasound's Liposuction Role Debated," http://molecularmedicine.medscape.com/IMNG/SkinAllergyNews/19.../san3003.06.02.htm, Mar. 17, 2000, pp. 1–2.

Eisenhauer, K., "6/24–Ultrasound Liposuction," http://www.channel6000.com/health/health–990624–191707.html, Mar. 17, 2000, pp. 1–2.

Nigro, D.M., "Ultrasound Assisted Lipoplasty (Liposuction)," http://www.drnigro.com/dennis.htm, Mar. 17, 2000, p. 1.

"Glossary," http://www.lipoinfo.com/glossary.htm, Mar. 17, 2000, pp. 1–14.

"Body Sculpting/Liposuction," http://www.cosmeticdoctor.com/sculpting.htm, Mar. 17, 2000, pp. 1–3.

"External Ultrasonic Liposuction," http://www.lipoinfo.com/chap14.htm, Mar. 17, 2000, p. 1.

"For Ultrasonic Liposuction," http://www.ultrasonic–liposuction.com/index.html, Mar. 17, 2000, p. 1.

"Internal, External Ultrasound Aids Liposuction," http://surgery.medscape.com/IMNG/SkinAllergyNews/1998/v.29.n03/san2903.46.01.htm/l, Mar. 17, 2000, pp. 1–3.

"Liposuction," http://www.ultrasonic–liposuction.com/informationA.html, Mar. 17, 2000, pp. 1–2.

"Liposuction," http://www.swmed.edu/home_pages/library/consumer/liposuc.htm, Mar. 17, 2000, p. 1.

"Liquefying the fat: Ultrasound Expands Score of Liposuction," http://www.swmed.edu/home_pages/new/liquilip.htm, Mar. 17, 2000, pp. 1–2.

"The Lipo Symposium," http://liposymposium.com/details/History/, Mar. 17, 2000, p. 1.

"Trends in Cosmetic Surgery: Lipoplasty (Liposuction)," http://www.wrc–gbmc.org/4rd.html, Mar. 17, 2000, p. 1.

"Ultrasound Liposuction (or Ultrasound Assisted Lipoplasty –UAL," http://www.ultrasonic–liposuction.com/InformationD.html, Mar. 17, 2000, pp. 1–2.

"Ultrasound Assisted Lipoplasty," http://www.plasticsurgery.org/surgery/ual.htm, Mar. 17, 2000, pp. 1–4.

"Ultrasound –Assisted Liposuction," http://www.drhobar.com/ual.htm, Mar. 17, 2000, pp. 1–4.

"Ultrasonic–Assisted Liposuction," http://www.liposymposium.com/details/procedure/techniques/UAL/, Mar. 17, 2000, pp. 1–2.

"Ultrasound–Assisted Liposuction," http://www.providence–hospital.org/technology/lipo.htm, Mar. 17, 2000, p. 1.

"Ultrasonic Liposuction; Body Contouring," http://www.drloomis.com/serv01.htm, Mar. 17, 2000, pp. 1–2.

* cited by examiner

SYSTEMS AND METHODS FOR ULTRASOUND ASSISTED LIPOLYSIS

This application is a continuation-in-part of application Ser. No. 09/753,273, filed Dec. 27, 2000, the disclosure of which is expressly incorporated herein by reference.

FIELD OF INVENTION

The present invention relates generally to systems and methods for destroying tissue using focused ultrasound, and more particularly to systems and methods for destroying tissue by focusing ultrasound from an external source towards subcutaneous tissues, such as adipose tissue to aid in body contouring.

BACKGROUND

Liposuction is a commonly used cosmetic surgical procedure for removing fat (adipose) cells to achieve a more desirable body shape. Liposuction usually involves an invasive surgical procedure, which includes penetrating the skin, melting or shearing the adipose tissue, and mechanically removing the adipose tissue using a vacuum or other suctioning device.

Tumescent liposuction is a common variation in which "tumescent" solution is introduced into a target tissue region, e.g., a layer of fatty tissue, to loosen the structure of the fatty tissue and to facilitate its suction. The tumescent solution generally includes, among other possible ingredients, a topical anesthetic, such as lidocaine, and a vasoconstrictor to reduce bleeding, such as Norinephrine. Generally, a large quantity of tumescent solution is infiltrated, e.g., in a one-to-one ratio with the fat to be removed, causing the tissue region to swell. Suction is then performed using a special cannula connected to a vacuum system that is introduced into the fatty layer through incisions in the patient's skin, typically three to six millimeters (3–6 mm) wide. The cannula is moved around inside each incision to reach target sites within the tissue region that are to be removed.

Traditional liposuction, however, is an extremely invasive, possibly traumatic procedure. As the cannula is moved through the tissue region, it may damage nerves and/or blood vessels, as well as the fatty tissue. Thus, complications include excessive bleeding, creating a significant risk of morbidity and/or mortality. Another potential problem with liposuction is lack of uniformity of the patient's final shape due to irregular removal of the fatty tissue.

In recent years, ultrasound has been suggested for assisting in liposuction procedures. For example, ultrasound assisted liposuction ("UAL") involves introducing a solid stick ultrasound transducer through an incision in the patient's skin and moving the transducer through a fatty tissue region. The transducer emits ultrasonic energy, generally at frequencies of 20–30 kHz, that may heat the tissue in the region until necrosis occurs, and/or may cause cavitation, thereby rupturing adipose cells in the region. Subsequently, a cannula is introduced into the tissue region to perform suction, as described above. Alternatively, a hollow transducer may be used that provides suction simultaneously with the delivery of ultrasonic energy.

One problem associated with known UAL techniques, however, is that the transducer may become quite hot during its use. This may result in damage or destruction of tissues adjacent to the target region by overheating or melting. To protect tissue outside the target region, the transducer may be introduced through the skin using an insulated sleeve, although this may require a much larger incision, e.g., about ten millimeters (10 mm) or more wide. In addition, the doctor may need to use extreme care and keep moving the transducer in order to avoid burning tissue. Finally, treatment may also be limited to direct contact between the transducer and the adipose tissue, possibly resulting in non-uniform destruction of fat cells in the target region.

As an alternative to UAL techniques, U.S. Pat. No. 5,884,631, issued to Silberg, discloses using an external ultrasonic generator to transmit ultrasound waves through a patient's skin to underlying adipose tissue. Silberg proposes using ultrasonic energy at a frequency above about twenty kilohertz to disrupt the connective tissue between fat cells, whereupon conventional liposuction may be used to remove the cells. The ultrasound energy in Silberg, however, is not focused, but instead is delivered from a point contact on the surface of a patient's skin indiscriminately into the underlying tissue. Such unfocused ultrasonic energy may be ineffective for facilitating liposuction since the energy is merely diffused generally into the underlying tissue.

In addition, noninvasive methods have been proposed for removing adipose tissue. For example, U.S. Pat. No. 5,143,063, issued to Fellner, discloses a device and method for necrosing adipose tissue by directing radiant energy directly to a tissue region or work site. Although Fellner generally discloses the use of radiant energy, such as radio frequency, microwave, or ultrasonic energy, the only specific examples given for focusing ultrasonic energy at a subcutaneous tissue region involve using a concave lens or a Barone reflector. Such a lens or reflector, however, may have a fixed "focal distance," i.e., the distance from the device to the "focal zone," i.e., the region to which the energy is focused. In addition, such devices may only generate a relatively small focal zone having a fixed size and shape.

In addition, the exemplary procedure suggested by Fellner involves focusing energy at a work site for at least about thirty to forty minutes in order to effectively heat and necrose tissue at the work site. Thus, the suggested procedures may be time-consuming and/or may risk heating or damaging tissue outside the work site.

Accordingly, systems and methods for destroying subcutaneous tissue and/or for providing more precise monitoring and/or guidance of focused ultrasonic energy used to remove adipose cells or other tissue would be considered useful.

SUMMARY OF THE INVENTION

The present invention relates generally to systems and methods for focusing ultrasound energy from a location external to a patient to rupture or otherwise remove cells, such as adipose cells, within a subcutaneous tissue region. The present invention may minimize damage, such as that caused by invasive surgical procedures and/or by heating of neighboring tissues when unfocused ultrasound is indiscriminately introduced into a tissue region. The target cells, preferably adipose cells, may be ruptured and then removed, for example, by natural excretion mechanisms within the body or by gentle suction.

In a preferred method, a transducer is disposed externally adjacent to the patient's skin. The transducer is driven with drive signals such that the transducer emits acoustic energy, while the acoustic energy is focused at a focal zone within a target tissue region. The acoustic energy, preferably ultrasonic energy, has sufficient intensity to vibrate, cavitate, and/or otherwise mechanically damage fluid within the focal zone, thereby rupturing or otherwise destroying tissue, e.g., adipose cells, within the focal zone. The ultrasonic energy is preferably applied using a relatively low duty cycle, i.e., in short bursts relative to the time between successive bursts to limit the amount of heating of tissue in and around the target tissue region. For example, the transducer may be operated using a duty cycle of about twenty percent (20%) or less, preferably about ten percent (10%) or less, and more preferably about one percent (1%) or less. Preferably, the transducer may emit ultrasonic energy at a frequency range between about two and ten megahertz (2–10 MHz), and more preferably between about four and six megahertz (4–6 MHz).

Various embodiments are contemplated for a transducer in accordance with the present invention. The transducer may have either a fixed focal distance or a variable focal distance. "Focal distance" is the distance from an acoustic emission surface of the transducer to a center of the "focal zone," i.e., the region where energy from the transducer is focused. In a preferred embodiment, the transducer is preferably configured for producing a substantially linear focal zone. The transducer may have a single transducer element, thereby having a fixed focal distance. For example, a single partial cylindrical transducer may be provided that focuses ultrasonic energy due to its geometry, or a substantially planar transducer may be provided that includes a lens for focusing the ultrasonic energy at a desired focal zone.

Alternatively, the transducer may include a phased array. For example, the transducer may include a plurality of linear transducer elements disposed adjacent to one another, e.g., in a partial cylindrical arrangement or in a substantially planar arrangement. Alternatively, the transducer may include a plurality of transducer elements defining respective portions of a single arc, each of which is projected onto a plane. Thus, the plurality of transducer elements may be arranged in a configuration similar to a Fresnel lens. Such a transducer configuration may substantially minimize the space between the acoustic emission surface of the transducer and the patient's skin, facilitating acoustically coupling the transducer to the patient and/or minimizing air gaps between the transducer and the patient's skin.

Drive circuitry is coupled to each individual transducer element, the drive circuitry being controlled by a controller. Drive signals from the drive circuitry cause the transducer element(s) to emit ultrasonic energy. The controller may control a phase shift value of respective drive signals to the transducer elements, thereby adjusting a focal distance to the focal zone.

In yet further embodiments, a transducer array may be provided that generates multiple simultaneous focal zones. These systems may include a plurality of individual transducers that are disposed side-by-side in a substantially planar configuration, thereby being capable of generating a plurality of substantially parallel linear focal zones. Treatment time may be decreased with such a multiple-focal zone embodiment, as will be appreciated by those skilled in the art.

In accordance with another aspect of the present invention, a transducer may be provided that includes one or more detectors for measuring ultrasound signals produced during cavitation. Generally, cavitating gas bubbles produce a strong signal, for example, at a frequency of approximately one half of the transmitted ultrasound waves. An acoustic sensor, such as a cavitation strip detector, may be provided on the transducer for detecting such cavitation signals.

A monitoring system may be coupled to the detector for monitoring cavitation during a procedure. For example, the system may include a processor that correlates the cavitation signals to determine the extent of cavitation, and consequently tissue destruction, occurring in the target tissue region. Preferably, a rate of change in amplitude of the detected signals may be monitored to determine when cells within a target tissue region have been substantially destroyed. Alternatively, the amplitude of the cavitation signals may be integrated over time until a predetermined value is reached. In addition or alternatively, the system may monitor the cavitation signals to ensure that a predetermined peak amplitude, i.e., rate of cavitation, is not exceeded, e.g., to provide a desired safety factor against excessive cavitation, which may be harmful to the patient.

Additionally, in accordance with another aspect of the present invention, an apparatus may be provided for moving an ultrasound transducer (or a set of transducers) in a controlled manner. For example, the transducer may be mounted to a frame that may be disposed adjacent the patient's skin. The transducer may be moved along the patient's skin, e.g., continuously or incrementally, to cavitate successively adjacent tissue regions, thereby providing a more uniform treatment.

Other objects and features of the present invention will become apparent from consideration of the following description taken in conjunction with the accompanying drawings.

DETAILED DESCRIPTION

Figure 1:
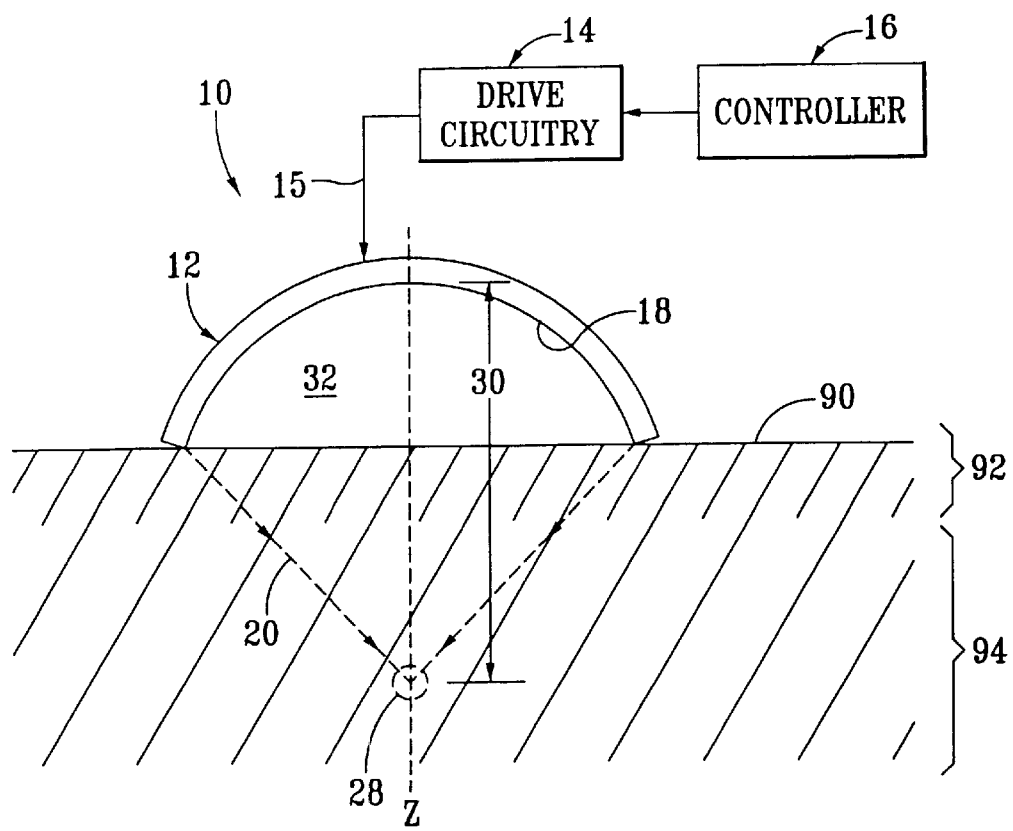
FIG. 1 is a schematic view of a first preferred embodiment of a transducer and system for treating tissue, in accordance with the present invention.
Figure 2:
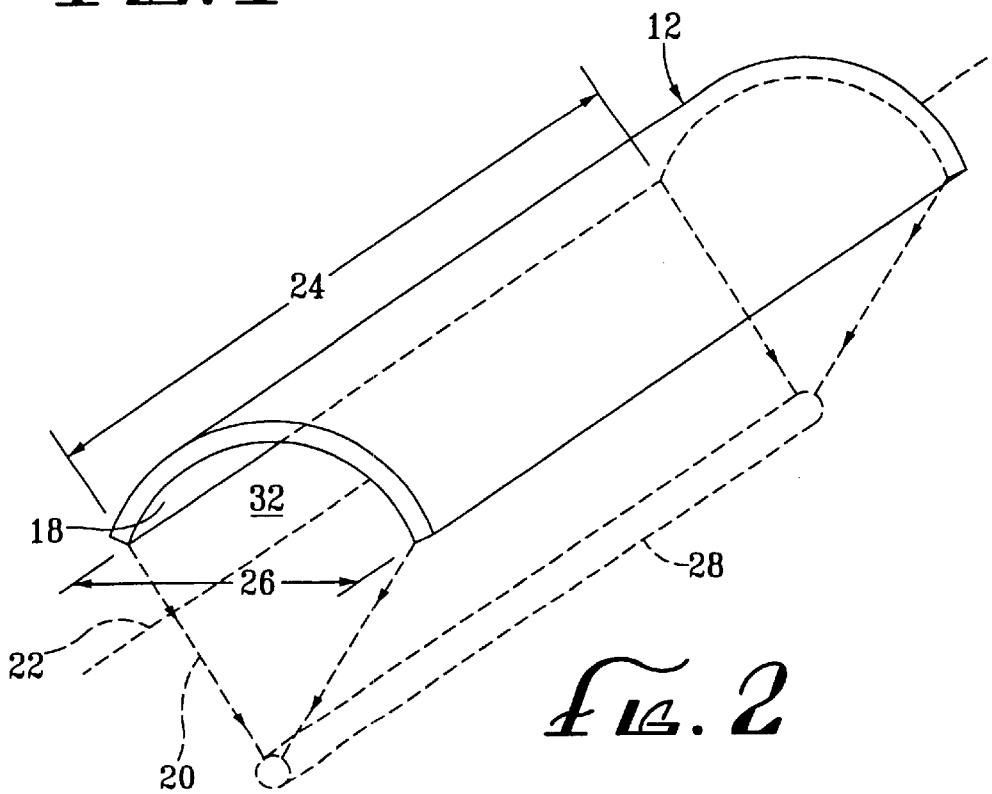
FIG. 2 is a perspective view of the transducer of FIG. 1.

Turning to the drawings, FIGS. 1 and 2 show a first preferred embodiment of a system 10 for treating tissue, in accordance with the present invention. Generally, the system 10 includes a transducer 12, drive circuitry 14 coupled to the transducer 12, and a controller 16 coupled to the drive circuitry 14.

The transducer 12 is generally made from piezoelectric material in a conventional manner, as is well known to those skilled in the art. When the transducer 12 is excited by electrical drive signals 15, the transducer 12 may emit acoustic energy from surface 18, as illustrated by exemplary acoustic waves 20. In the preferred embodiment shown, the transducer 12 has a single transducer element defining an arcuate cross-section that extends substantially parallel to a longitudinal axis 22 of the transducer 12. Thus, the surface 18 defines a portion of a cylinder, preferably having a substantially constant radius of curvature. Alternatively, the cross-section of the surface 18 may define a portion of another generally concave curve. The term "partial cylindrical" as used herein is intended to include any such variations even if they define less than half of a cylinder and/or do not have a constant radius of curvature. In a preferred embodiment, the transducer 12 preferably has a base length 24 of between about five and fifteen centimeters (5–15 cm), and a base width 26 of between about one and four centimeters (1–4 cm).

Due to the partial cylindrical shape of the transducer 12, the acoustic energy emitted from the surface 18 converges at a focal zone 28. Preferably, the focal zone 28 has a substantially linear shape that extends substantially parallel to the longitudinal axis 22, as described further below. Because the transducer 12 has only a single transducer element, a "focal distance" 30, i.e., a distance from the surface 18 to a center of the focal zone 28 along axis "z," is substantially fixed by the geometry of the transducer 12. For example, for a constant radius transducer, the focal distance 30 may correspond substantially to a geometric focus of the transducer 12.

The drive circuitry 14 is coupled to the transducer 12 and provides drive signals 15 to the transducer 12 that cause the transducer 12 to emit acoustic energy. Preferably, radio frequency (RF) drive signals 15 are used to excite the transducer 12 to emit ultrasonic energy at a predetermined amplitude, frequency, and wave shape. In a preferred embodiment, the drive signals 15 cause the transducer 12 to emit ultrasonic energy at a frequency between about two and ten Megahertz (2–10 MHz), and more preferably between about four and six Megahertz (4–6 MHz). The optimal frequency may be dependent upon the focal distance of the focal zone generated by the transducer. For example, if a longer focal distance is needed, relatively lower frequency drive signals may be preferred, e.g., to minimize dissipation in the intervening tissue, while for a relatively shorter focal distance, higher frequency drive signals may be preferred.

The controller 16 is coupled to the drive circuitry 14 and controls various aspects of the drive signals 15 provided by the drive circuitry 14. For example, the controller 16 may adjust an amplitude of the drive signals 15, and consequently the amplitude of the acoustic waves 20. Preferably, as described further below, the controller 16 directs the drive circuitry 14 to cause the transducer 12 to emit acoustic energy at an amplitude or intensity sufficient to vibrate, cause cavitation, and/or otherwise cause mechanical damage, thereby destroying tissue, e.g., rupturing adipose cells, in the focal zone 28.

In a preferred embodiment, the controller 16 activates the drive circuitry 14 such that the transducer 12 emits acoustic energy using a relatively low "duty cycle," i.e., a ratio between a time period that the transducer 12 is activated during a cycle and a time period of each cycle. For example, the duty cycle may be about twenty percent (20%) or less, preferably about ten percent or less, and more preferably about one percent or less. Thus, the transducer may emit acoustic energy in relatively short bursts, each burst including only a few discrete wavelengths of acoustic energy, but having sufficient intensity to cause cavitation and destroy tissue within the focal zone. For example, short-burst pulses may have a duration of between approximately 0.25 and 20 $\mu$sec may be emitted every 100 $\mu$sec during a single sonication. Because the acoustic energy is highly focused and of sufficient amplitude, these short bursts are adequate to rupture or otherwise destroy cells, e.g., adipose cells, in the focal zone 28. Thus, while the acoustic energy radiated during a single burst is relatively high, the time-average acoustic energy emitted by the transducer is relatively low, thereby minimizing the risk of heat build-up in or adjacent to the target tissue region, contrary to previously known hyperthermia techniques that use heating to necrose tissue.

The transducer 12 is generally disposed in direct contact with a patient's skin 90. Gel or other acoustically conductive media (not shown) may be provided between the transducer 12 and the patient's skin 90 to acoustically couple them. Preferably, the acoustic gel fills a hollow space 32 between the transducer 12 and the patient's skin 90 to prevent discontinuities or irregularities in the ultrasonic energy emitted by the transducer 12 that passes through the patient's skin 90.

Alternatively, the transducer 12 may be disposed within a casing, such as a flexible bag (not shown). An outer surface of the casing may be formed from an acoustically transparent material, such as a thin plastic sheet of mylar or polyvinyl chloride (PVC). More preferably, the outer surface may be substantially flexible to facilitate the casing conforming to the shape of a surface contacted by the casing, such as a patient's skin. The casing may be filled with degassed water, gel, or other acoustically conductive fluid to facilitate acoustically coupling the transducer to the patient's skin, as is well known in the art. Additional information on such a transducer and casing may be found in U.S. Pat. No. 5,526,814, the disclosure of which is expressly incorporated herein by reference.

As best seen in FIG. 1, during a lipolysis procedure, the transducer 12 is generally placed externally adjacent to the patient's skin 90. Gel or other acoustically conductive material (not shown) is placed between the transducer 12 and the patient's skin 90, as described above. Alternatively, if the transducer 12 is provided in a casing (not shown), the outer surface of the casing may be placed in contact with the patient's skin 90, possibly with water, gel, or other acoustically conductive material placed between the casing and the patient's skin 90 to provide additional acoustical coupling, if desired. The acoustically conductive material may act as a spacer to allow focusing of the acoustic energy at different depths within the tissue, as described further below.

The patient's skin 90 includes a layer of epidermis overlying a layer of dermis 92, which, in turn, generally overlies a subcutaneous tissue layer including fatty (adipose) tissue 94. The transducer 12 is positioned a predetermined distance above the patient's skin 90 such that the focal zone 28 of the transducer 12 is positioned within the subcutaneous tissue region 94. For example, if the transducer 12 is mounted in a casing, the casing may be sufficiently flexible to accommodate a range of positions above the patient's skin 90 without decoupling the casing from the patient's skin 90.

The transducer 12 is then activated, causing acoustic energy to penetrate through the epidermis and dermis 92 into the fatty tissue layer 94, and converge substantially at the focal zone 28. Preferably, during a "sonication," i.e., a single treatment during which acoustic energy is focused at a target tissue region for a set time period, the transducer 12 may be activated for a plurality of successive relatively short bursts, as described above, to substantially destroy the tissue in the focal zone 28.

"Cavitation" is a well-known phenomenon experienced when acoustic energy encounters matter. Generally, the acoustic energy causes gas bubbles dissolved in fluid within the tissue to "pop," thereby releasing kinetic energy. For example, the acoustic energy may be absorbed by water in tissue, causing gas bubbles dissolved in the water to rapidly contract and expand, and consequently explode or "pop." Alternatively, other existing gas bubbles occurring within the tissue may be cavitated using acoustic energy. The released kinetic energy may rupture cells or loosen connective tissue adjacent to the cavitated gas bubbles.

In a further alternative, gas bubbles, e.g., dissolved in a liquid, may be introduced into the target tissue region before the transducer 12 is activated. For example, a "tumescent" solution may be injected into the target tissue region that includes gas bubbles, such as air or Nitrogen, dissolved therein. The tumescent solution may also include a variety of known materials that may enhance a lipolysis procedure. For example, the tumescent solution may include a topical anesthetic, such as lidocaine, or a vasoconstrictor, such as Norinephrine. Thus, in addition to providing gas bubbles to promote cavitation, the tumescent solution may help reduce pain to the patient, may reduce bleeding, may cause tissue within the target tissue region to swell, may help loosen fatty tissue, and the like, as is well known in the art.

The tumescent solution may be injected into the target tissue region before the transducer is positioned adjacent the patient's skin. If the ultrasound treatment is to be followed by gentle suction, large quantities of tumescent solution may be infiltrated into the tissue, for example, in a one-to-one or less ratio with the fat tissue to be removed, e.g., to loosen the tissue. The kinetic energy released by the cavitating gas bubbles preferably causes the walls of cells in the focal zone, such as adipose cells, to rupture, releasing cell media into the interstitial space between the cells, e.g., causing the subcutaneous adipose tissue 145 to become emulsified. The transducer 12 may then be moved to another location, for example, adjacent to the first target tissue region, and the procedure repeated.

Alternatively, other gas bubble-containing fluids may be introduced. For example, ultrasound contrast agents, such as liquids including microspheres containing lipids or other materials, may be injected into the tissue region. In a further alternative, free gas bubbles suspended in a liquid may be injected.

In yet a further alternative, the mechanical energy imposed on the cells from the acoustic energy may be of sufficient intensity that the resulting mechanical damage may cause the cells to rupture, either with or without cavitation also occurring. Thus, cavitation is merely a specific example of mechanical damage that may be imposed by the acoustic energy upon the cells in order to cause the cells to rupture.

Preferably, the transducer 12 is successively moved incrementally or continuously in a direction substantially perpendicular to its longitudinal axis 18 and activated, thereby causing cavitation through a layer of subcutaneous tissue. To assist in this method, the transducer 12 may be a movably mounted to a frame 650, such as that shown in FIG. 12, and described further below. This may allow the target cells to be ruptured in a substantially uniform manner until a generally planar layer of subcutaneous tissue, e.g., a layer of adipose tissue, is cavitated.

Figure 3:
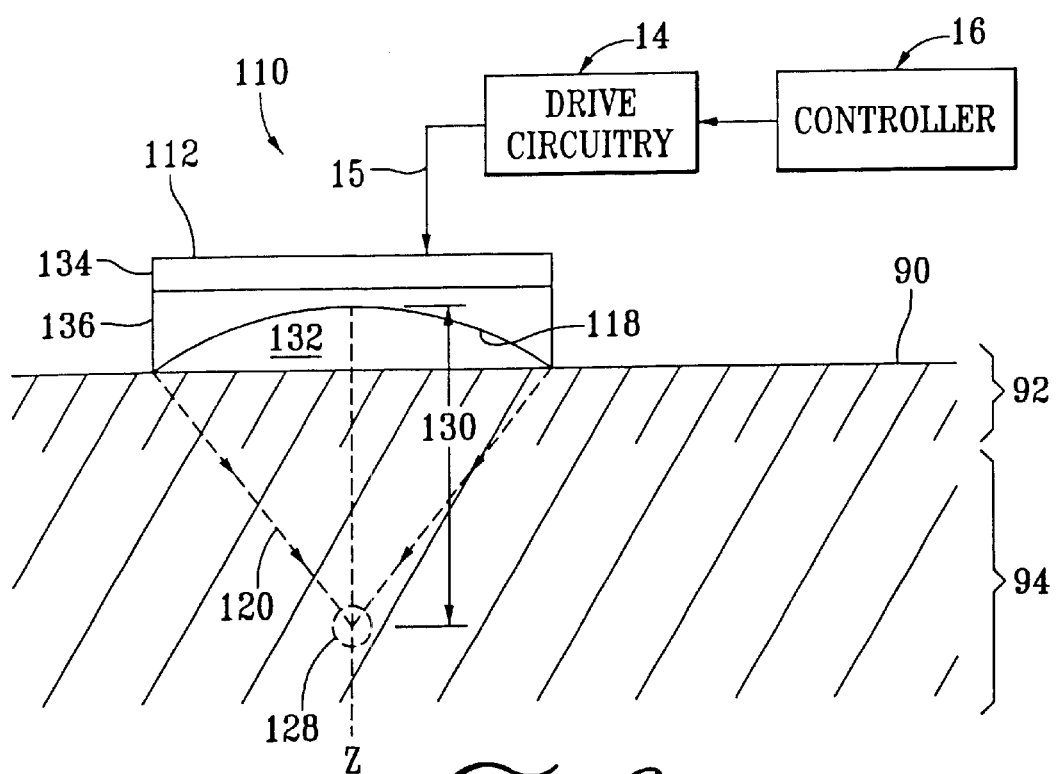
FIG. 3 is a schematic view of a second preferred embodiment of a transducer and system for treating tissue, in accordance with the present invention.
Figure 4:
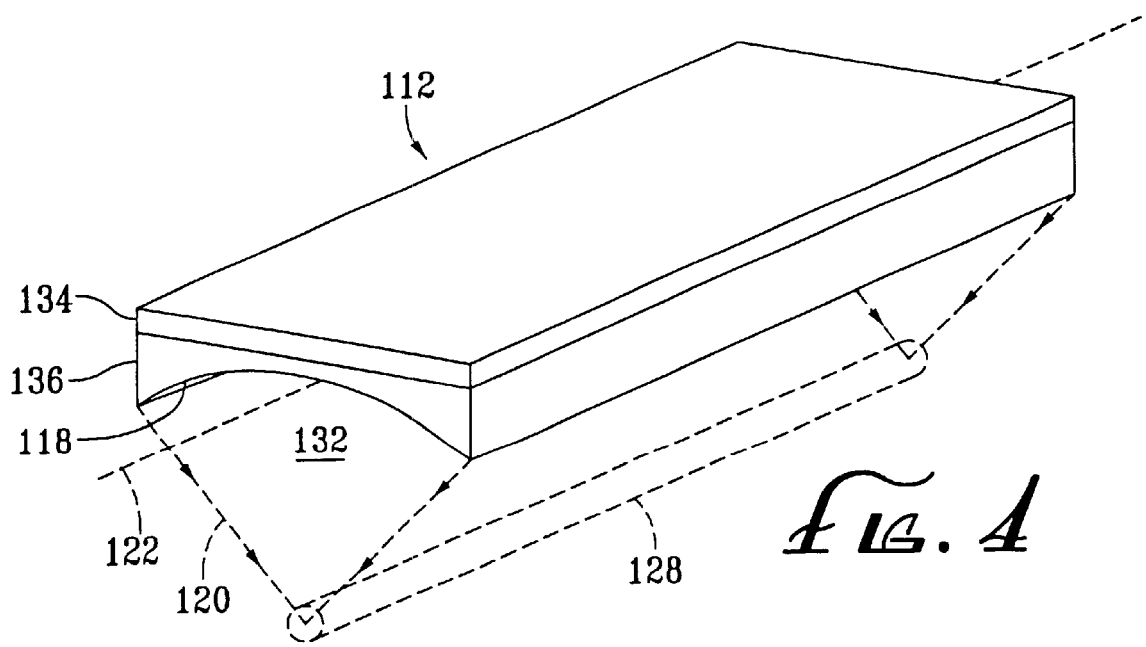
FIG. 4 is a cross-sectional view of the transducer and lens of FIG. 3.

Turning to FIGS. 3 and 4, an alternative embodiment of a system 110 in accordance with the present invention is shown that includes a transducer 112 having a single, substantially planar transducer element 134 and an acoustic lens 136. The system 110 also includes drive circuitry 14 and a controller 16, similar to the embodiment described above. The lens 136 is acoustically coupled to the transducer element 134, thereby focusing ultrasonic energy, represented by exemplary waves 120, emitted by the transducer element 134 at a focal zone 128. The lens 136 may be substantially permanently or detachably attached to the transducer element 134. Alternatively, the lens 136 may be spaced a predetermined distance from the transducer element 134, and an acoustically conductive material may be disposed between the transducer element 134 and the lens 136.

Preferably, the lens 136 defines a partial cylindrical emission surface 118, more preferably having an elongate concave shape, for focusing the acoustic energy generated by the transducer element 134 at a substantially linear focal zone 128 that extends substantially parallel to a longitudinal axis 122 of the transducer 112. In the preferred embodiment shown, the lens 136 has an elongate concave emission surface 118, although alternatively an elongate convex emission surface (not shown) may be provided depending upon the material of the lens 136. Because a focal distance 130 to the focal zone 128 is substantially fixed by the geometry of the lens 136, the transducer 134 may be moved closer or farther away from the patient's skin 90 to change the location of the focal zone 128 within the subcutaneous tissue region 94. In an alternative embodiment, the lens 136 may be replaced with another lens (not shown) having a different radius of curvature, to provide a desired focal distance 130 to the focal zone 128. In a further alternative, an acoustic lens may be provided that allows adjustment of the focal distance, such as that disclosed in co-pending application Ser. No. 09/557,185, filed Apr. 21, 2000, the disclosure of which is expressly incorporated herein by reference.

Figure 5:
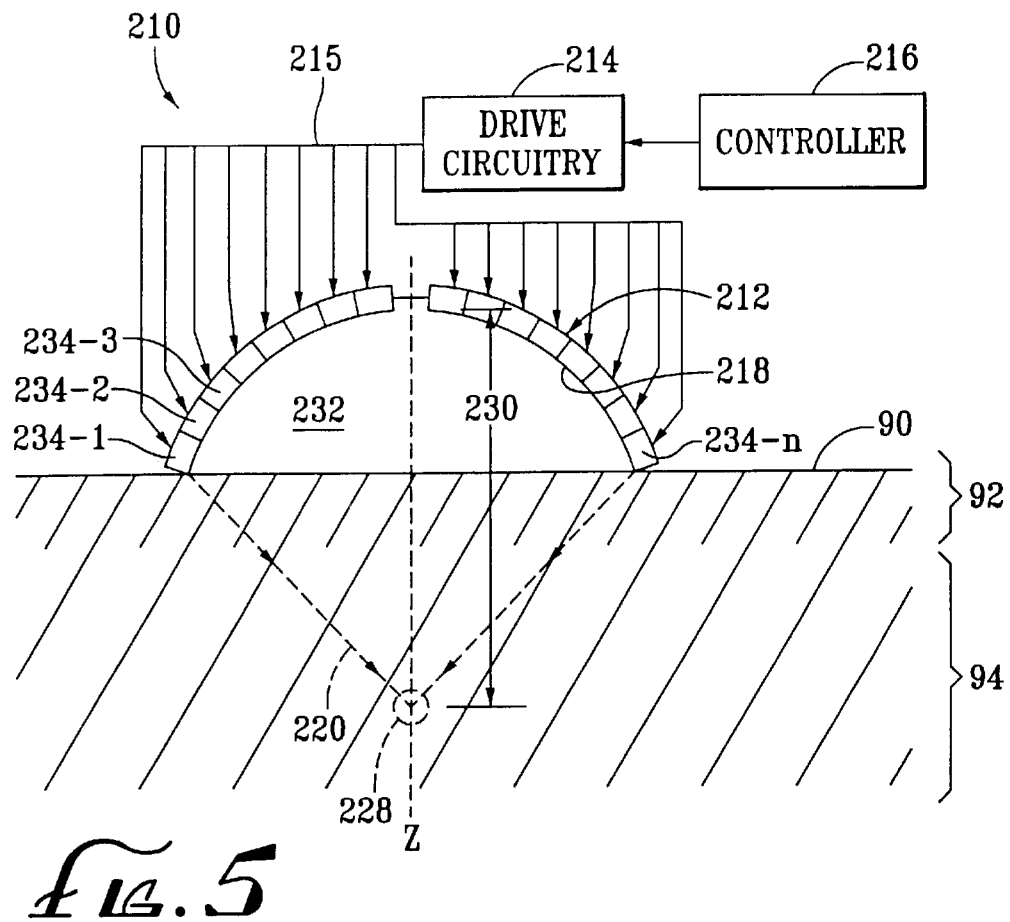
FIG. 5 is a schematic view of a third preferred embodiment of a transducer and system for treating tissue, in accordance with the present invention.
Figure 6:
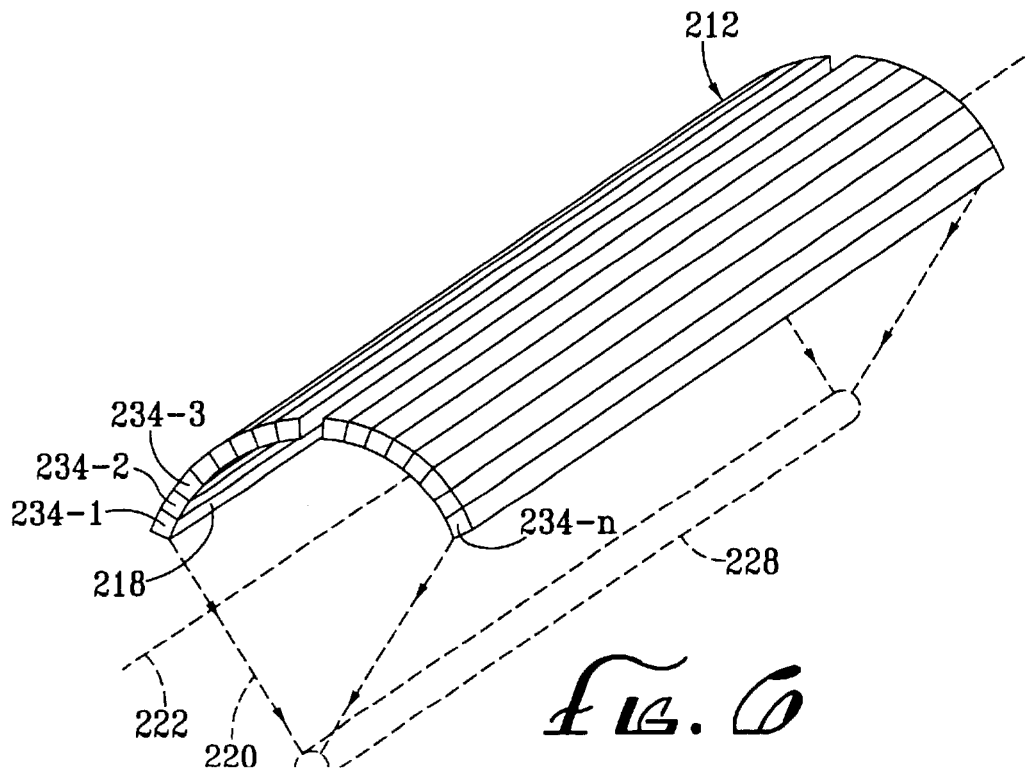
FIG. 6 is a perspective view of the transducer of FIG. 5.
Figure 7:
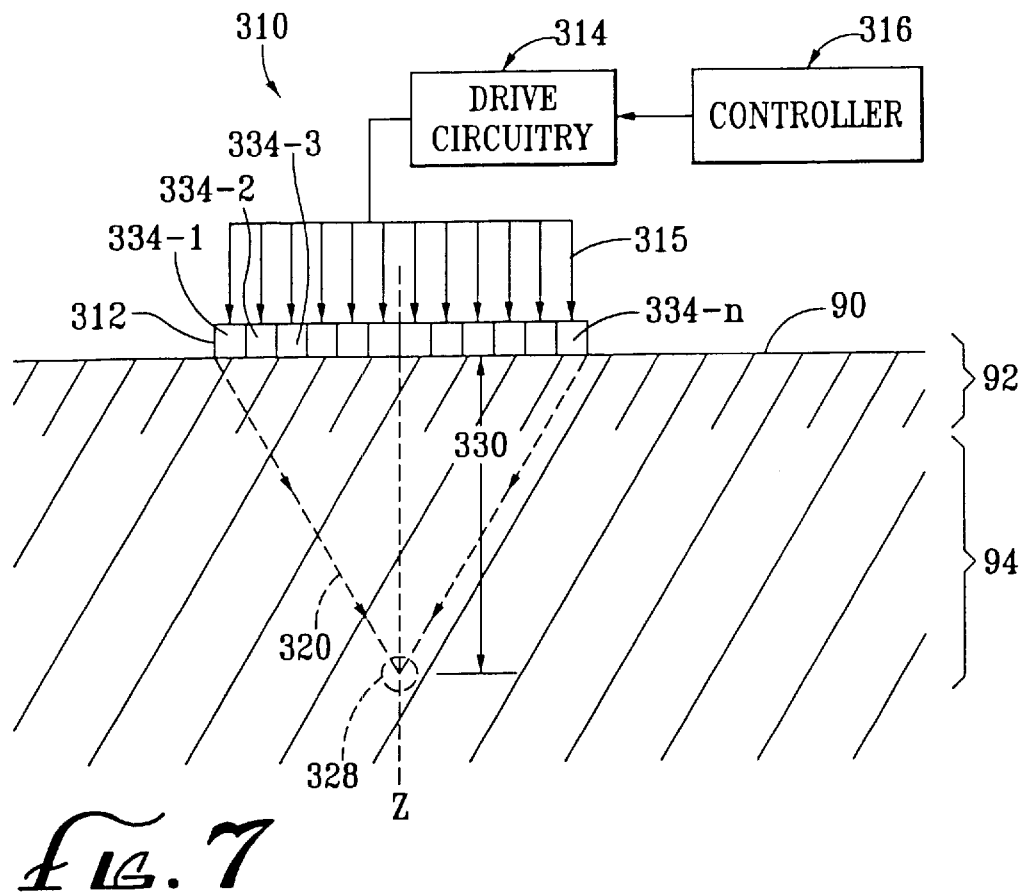
FIG. 7 is a schematic view of a fourth preferred embodiment of a transducer and system for treating tissue, in accordance with the present invention.
Figure 8:
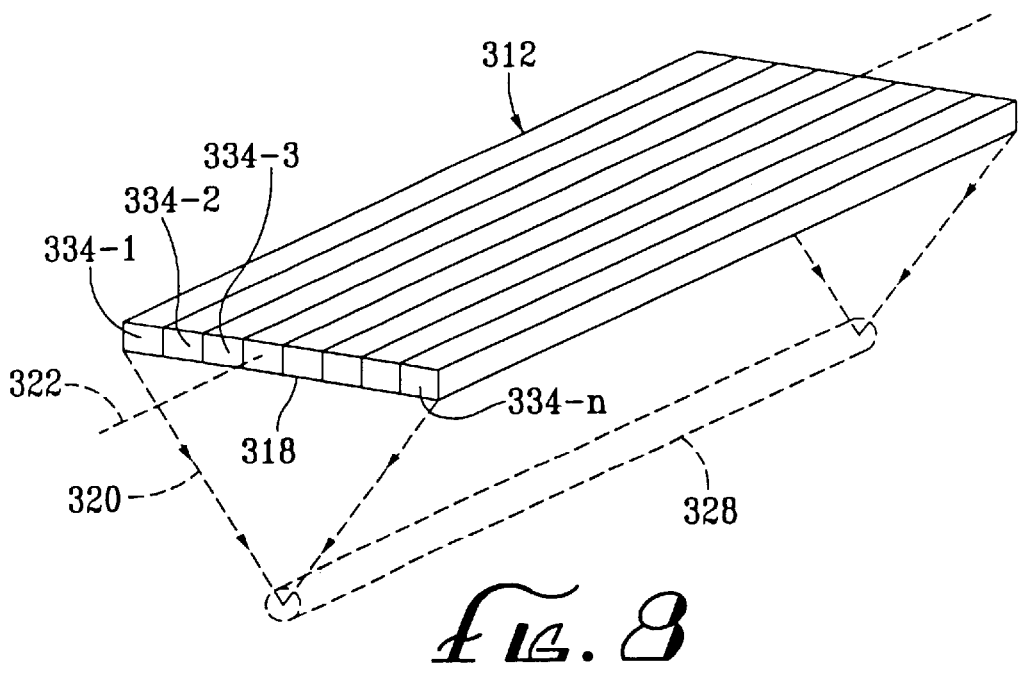
FIG. 8 is a perspective view of the transducer of FIG. 7.

Referring now to FIGS. 5 and 6, another preferred embodiment of a system 210 in accordance with the present invention is shown that includes a transducer 212, drive circuitry 214, and a controller 216. The transducer 212 includes a plurality of transducer elements (234-1 to 234-n), each transducer element 234 preferably extending substantially parallel to a longitudinal axis 222. More preferably, the transducer elements 234 are arranged in a linear configuration, i.e., side-by-side in a lengthwise manner, thereby together defining a partial cylindrical emission surface 218. In an alternative embodiment, shown in FIGS. 7 and 8, a transducer 312 may include a plurality of transducer elements 334 disposed in a substantially planar configuration extending substantially parallel to longitudinal axis 322.

The transducer 212 may be formed from a plurality of individual transducer elements 234 that are bonded together. Alternatively, the transducer 212 may be formed from a single piece of piezoelectric material, with grooves formed therein to separate and define each transducer element 234. Any spaces (not shown) between the transducer elements 234 may be filled with silicone and the like to substantially isolate the transducer elements 234 from one another, as is well known to those skilled in the art. The transducer 212 may include between about three and thirty, and preferably between three and ten, transducer elements 234.

The drive circuitry 214 is individually coupled to each transducer element 234 to deliver respective drive signals 215 to the transducer elements 234. The controller 216 is coupled to the drive circuitry 214 for controlling several aspects of the drive signals 215 generated by the drive circuitry 214. First, the controller 216 may control the amplitude of the drive signals 215, for example, to control the intensity of ultrasonic energy delivered by the transducer 212, similar to the embodiments described above. In addition, the controller 216 may control a phase shift value between each of the transducer elements 234. For example, by shifting the phase between the transducer elements 234-1 to 234-n, the focal distance 230 to the focal zone 228 may be adjusted along the z-axis. The controller 216 may include a processor, such as a microcomputer (not shown), that is coupled to the drive circuitry 214 for controlling these aspects of its operation.

Figure 9:
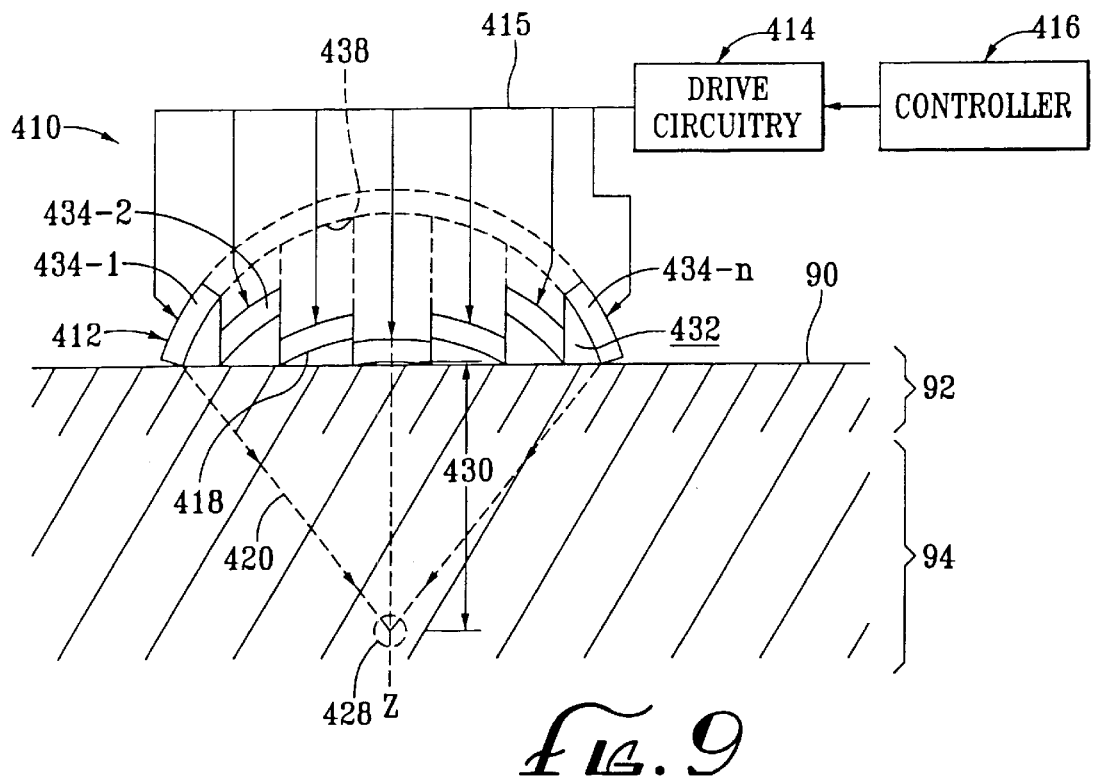
FIG. 9 is a cross-sectional view of another preferred embodiment of a multiple-element transducer array, in accordance with the present invention.

Referring now to FIG. 9, another embodiment of a system 410, in accordance with the present invention, is shown that includes a transducer 412, drive circuitry 414, and a controller 416. The transducer 512 includes a plurality of transducer elements 434-1 to 434-n formed from piezoelectric material, similar to the embodiments described above. The transducer elements 434 have a cross-section corresponding substantially to respective portions of a cylinder 438 (shown in phantom) that are projected generally onto a plane (defined by the surface of the patient's skin 90 in FIG. 9). Thus, the transducer 412 may include an emission surface 418 that corresponds substantially to a partial cylinder 438, but may substantially minimize a cavity 432 between the transducer 412 and the patient's skin 90. This configuration has a geometry somewhat similar to an optical lens, called a Fresnel lens, which is a transparent panel used to focus light passing through it.

The drive circuitry 414 is coupled to the individual transducer elements 434 for supplying drive signals 415, similar to the embodiments described above. The transducer 412 emits acoustic energy similar to the partial cylinder 438, with the discontinuity between adjacent transducer elements being substantially negligible. The distance that the transducer elements 434 are projected from the partial cylinder 438 may require compensation to ensure proper focusing. Preferably, the controller 416 controls the drive circuitry 414 to introduce phase shifts into the drive signals 415 to compensate for the distance between the transducer elements 434 and the portion of the partial cylinder 438 from which the respective transducer elements 434 are projected. Thus, the inner transducer elements 434-2 to 434-(n-1) may emit acoustic energy having predetermined delays relative to the outer transducer elements 434-1 and 434-n such that the acoustic energy delivered to focal zone 428 has similar properties to acoustic energy that would be emitted by the partial cylinder 438.

The transducer 412 may be placed in contact with a patient's skin 90, with acoustic gel or similar material provided within the cavity 432 to acoustically couple the transducer 412 to the patient. Because of the substantially planar configuration of the transducer 412, significantly less acoustic gel may be required, thereby reducing the possibility of discontinuities between the transducer 412 and the patient's skin 90. Acoustic energy may then be delivered through the epidermis and dermis 92 into a subcutaneous fatty tissue layer 94 and focused at focal zone 428. The controller 416 may introduce phase shifting to compensate for the transducer configuration, as well as providing further phase shifting to control a focal distance 430 and/or size and shape of the focal zone 428, similar to the embodiments described above.

In an alternative embodiment, a multiple element transducer device may be provided that is coupled to an acoustic lens having a configuration similar to a Fresnel lens. For example, a transducer device (not shown) may be provided that includes a substantially planar transducer array, such as that shown in FIGS. 7 and 8. A lens, configured similar to the transducer 412, may be coupled to the emission surface of such a transducer array to provide further focusing of acoustic energy emitted by the transducer array.

Figure 10:
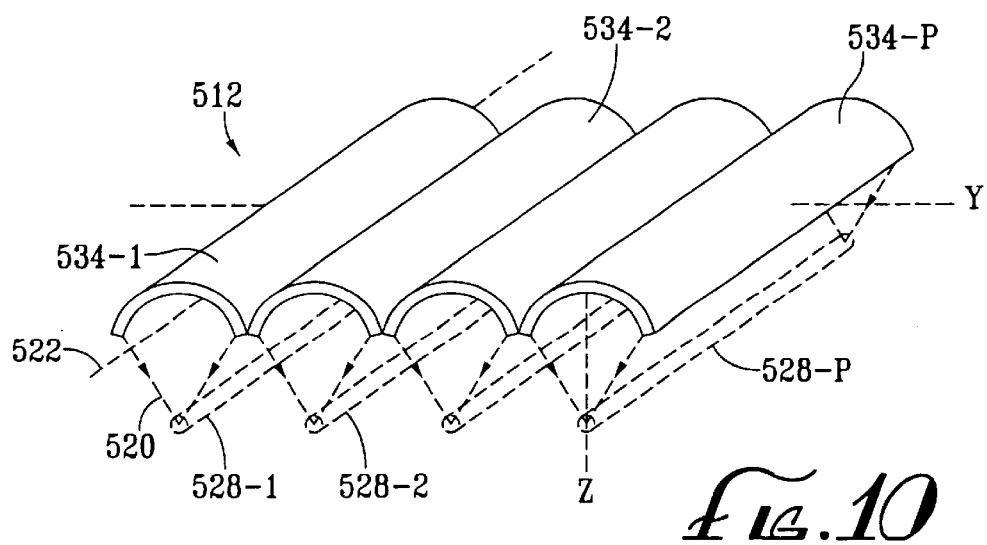
FIG. 10 is a perspective view of yet another preferred embodiment of a multiple-element transducer array, in accordance with the present invention.

Referring now to FIG. 10, an alternative embodiment of a transducer array 512 is shown that includes a plurality of transducers 534-1 to 534-p arranged side-by-side in a substantially planar configuration disposed substantially parallel to longitudinal axis 522. Each of the transducers 534 may be similar in construction to any of the transducers described above. The transducers 534 may be connected to one another and/or may be provided on a track, such as the frame described below.

During use, the transducer array 512 may be acoustically coupled to a patient (not shown), for example, by placing the transducers 534 in contact with or in close proximity to the patient's skin (also not shown). Any spaces between the transducers 534 and the skin may be filled with an appropriate acoustically conductive medium, such as an acoustic gel (not shown) that may have a density similar to the tissue being treated, e.g., adipose tissue. The transducers 534 may be activated to generate a plurality of substantially parallel focal zones 528-1 to 528-p. The transducer array 512 may be moved along the surface of the patient's skin, e.g., along a Y-axis, i.e., substantially perpendicular to the longitudinal axis 522 and z-axis, thereby rupturing or otherwise destroying a layer of tissue, e.g., a layer of adipose tissue (also not shown).

Figure 11:
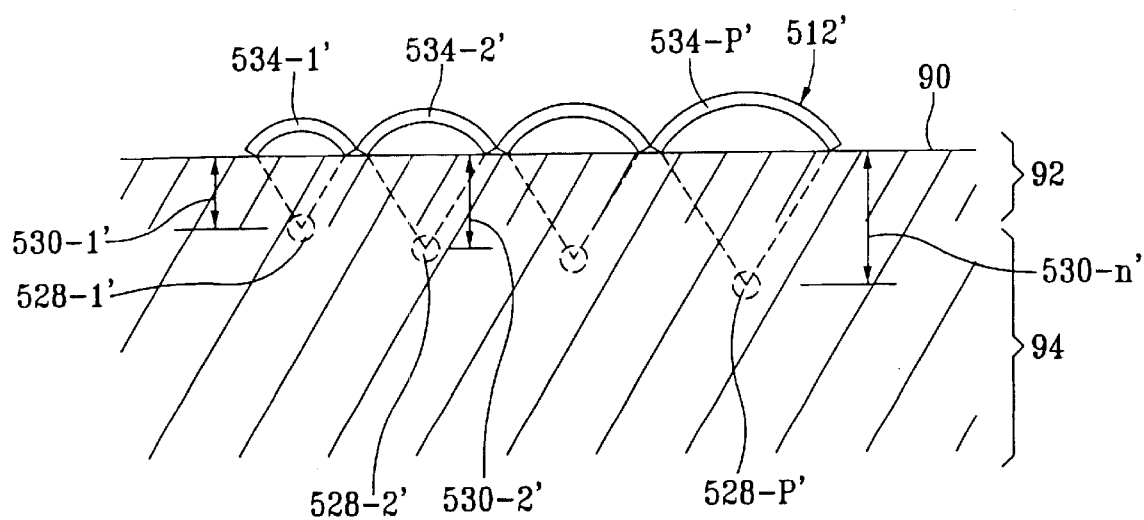
FIG. 11 is a cross-sectional view of an alternative embodiment of the transducer array of FIG. 10.

Thus, the transducer array 512 may only have to be moved a distance equal to a distance between adjacent transducers 534 in order to remove a layer of tissue beneath the transducer array 512. This may provide a significantly shorter treatment time than using a single transducer, as will be appreciated by those skilled in the art. Alternatively, as shown in FIG. 11, transducer array 512' may include a plurality of transducers 534-1' to 534-n' that have progressively deeper focal distances 530-1' to 530'n'. Thus, as the transducer array 512 is moved along a patient's skin 90, several layers of tissue within tissue region 94 may be substantially simultaneously cavitated.

In a further alternative, the transducer array may be provided within a fluid-filled casing (not shown), such as that described above, that may be placed in contact with a patient's skin. The transducer array may be moved within the casing, e.g. incrementally or continuously, substantially parallel to the surface of the patient's skin. Thus, a single layer or multiple layers of tissue may be removed without having to directly contact the patient's skin with the transducer or move the transducer directly along the patient's skin.

Figure 12:
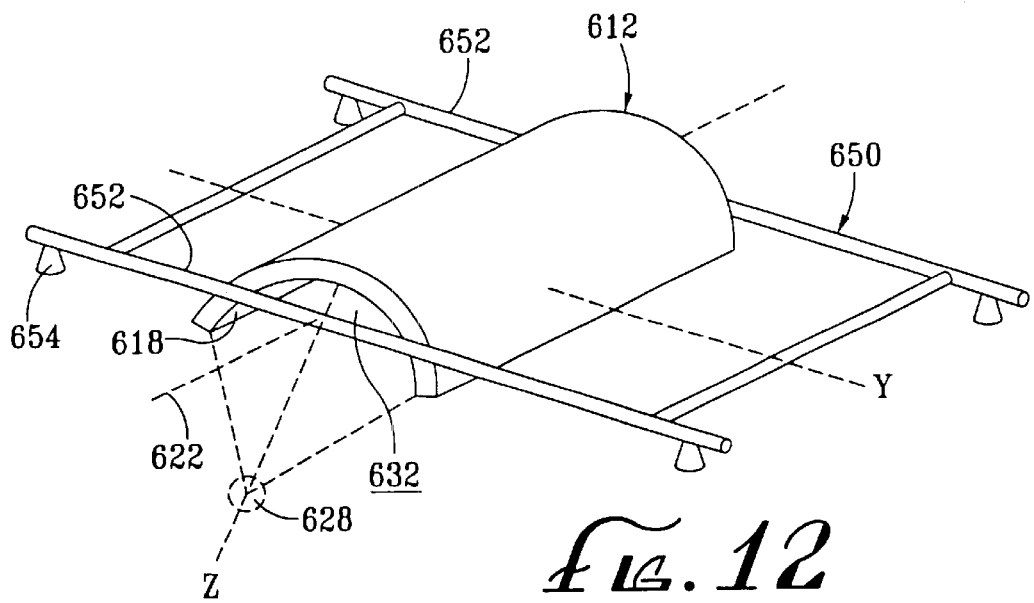
FIG. 12 is a perspective view of a partial cylindrical transducer movably mounted to a track, in accordance with yet another aspect of the present invention.

Turning to FIG. 12, the various embodiments of transducers described herein, designated generally as 612, may be movably mounted to a frame 650. The frame 650 may include a pair of spaced apart rails 652 extending along a Y-axis of the frame 650. The transducer 612 may be slidably mounted to the rails 652, for example, in tracks (not shown). Alternatively, the frame 650 may be mounted within a casing (not shown) as described above. Preferably, the frame 650 is substantially flat or is contoured similar to a corresponding region of a patient's body (also not shown). Thus, the transducer 612 may be moved along the rails while remaining substantially constantly in contact with the patient's body.

In one embodiment, the frame 650 may facilitate manual manipulation of the transducer 612 with respect to the patient's body. The transducer 612 may be coupled to the patient's skin (not shown), e.g., by providing acoustic gel and the like in the cavity 632 and/or elsewhere between the transducer 612 and the patient's skin. The transducer 612 may be moved along the frame 650 to a desired location, and then activated to cavitate or otherwise rupture cells of an underlying tissue region.

Figure 13:
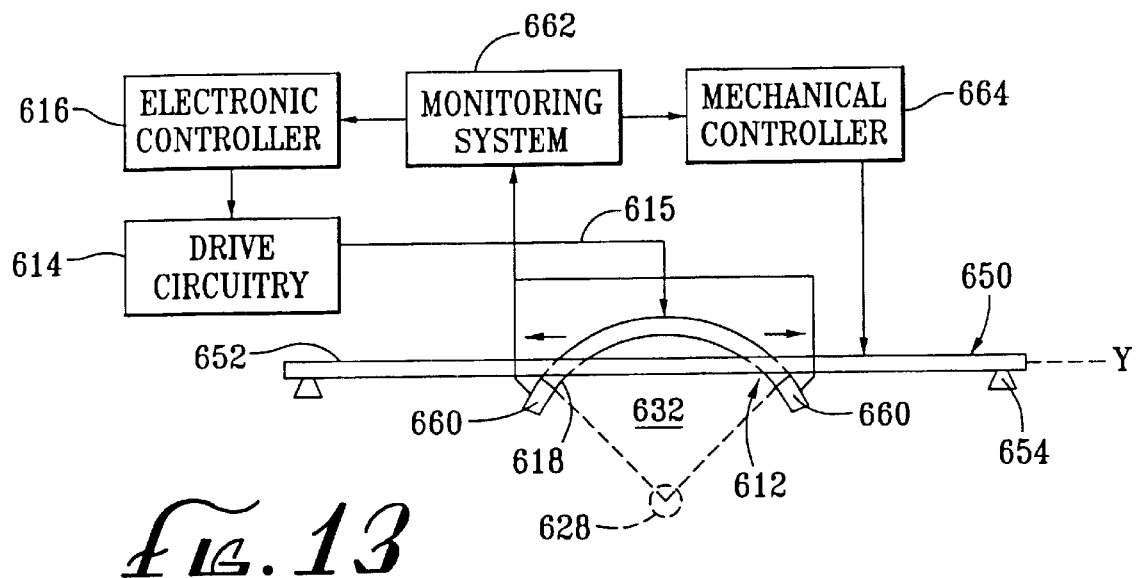
FIG. 13 is a cross sectional view of a system for treating tissue including cavitation detectors, in accordance with another aspect of the present invention.

Preferably, the frame 650 may facilitate motorized and/or automatic operation of the transducer 612. As shown in FIG. 13, a mechanical controller 664, e.g., including a motor (not shown), may be coupled to the frame 650, e.g., to the track (not shown) in the rails 652, or directly to the transducer 612. The controller 664 may allow the transducer 612 to be moved incrementally, continuously, and/or based upon desired feedback along the Y-axis, i.e., in a direction substantially perpendicular to a longitudinal axis 622 of the transducer 612. For example, the transducer 612 may be automatically moved to a desired location, activated for a predetermined time, moved to an adjacent location, activated again, and so on to destroy or remove a layer of tissue, e.g., to provide a more uniform lipolysis of a layer of adipose tissue.

In accordance with another aspect of the present invention, one or more cavitation detectors may be associated with any of the transducers described herein. The cavitation detectors may facilitate controlling a treatment, e.g., to more evenly and uniformly destroy a layer of tissue, or may be provided as a safety feature. Turning to FIG. 13, in a preferred embodiment, cavitation strip detectors 660 may be provided on opposing edges of a transducer 612. The detectors 660 may be between about one and two millimeters (1–2 mm) wide, and may extend substantially the entire length of the transducer 612. The detectors 660 may be coupled to a monitoring system 662, e.g., for monitoring cavitation within the focal zone 628 of the transducer 612.

In one embodiment, the monitoring system 662 includes a meter (not shown), which may provide an output, e.g., on a gauge or other display, based upon signals detected by the detectors 660. As gas bubbles in the focal zone are cavitated, they produce ultrasonic signals, and in particular, may produce relatively strong signals at approximately half of the frequency of the original or incident ultrasound waves. Alternatively, the meter may detect rupturing of the cells themselves, e.g., due to cavitation and/or other mechanical damage. The detectors 660 may be configured for detecting such cavitation signals produced at the focal zone 628 of the transducer 612. Thus, a physician performing a lipolysis procedure may monitor the cavitation signals using the detectors 660 to ensure that a desired level of cavitation is occurring and/or that a predetermined maximum level of cavitation is not exceeded.

Alternatively, the monitoring system 662 may be coupled to a controller 616 and/or drive circuitry 614 that are used to drive the transducer 612. For example, the monitoring system 662 may notify the controller 616 when a maximum level of cavitation is exceeded (which may be preset by the user), whereupon the controller 616 may direct the drive circuitry 614 to automatically discontinue drive signals 615 to the transducer 612. The controller 616 may then require resetting by the physician before the transducer 612 may be used for any further treatment, or the controller 616 may only discontinue the drive signals 615 for a predetermined time, e.g., to provide sufficient time for the tissue to recover. Thus, the detectors 660 may provide a desired safety factor during a treatment.

In a further alternative, the controller 616 may adjust an amplitude of the drive signals 615 in response to the cavitation signals detected by the detectors 660. The controller 616 may correlate the amplitude of the cavitation signals to an extent of cell destruction occurring at the focal zone 628. More preferably, the controller 616 may correlate a rate of change of amplitude of the cavitation signals over time to determine the extent that cells have been ruptured within the focal zone. Thus, if cavitation is occurring at too great a rate, which may excessively damage tissue in or adjacent to the focal zone, the amplitude of the drive signals 615 may be reduced accordingly.

In addition or alternatively, the monitoring system 662 may be coupled to a mechanical controller 664 for moving the transducer 612 within a frame 650. For example, the intensity of the cavitation signals, and preferably a rate of change in intensity of the cavitation signals may be correlated to an empirical database to automatically determine when a desired level of cell destruction has occurred within the focal zone 628. When a predetermined rate of change is detected, e.g., the rate of change begins to drop at a predetermined rate, the mechanical controller 664 may automatically move the transducer 612 to a new and/or adjacent location. Alternatively, the amplitude of the cavitation signals may be integrated over time until a predetermined value is reached, indicating that a desired level of cell destruction has occurred. The drive signals 615 to the transducer 612 may be discontinued until the transducer 612 is moved to the new location.

Thus, for example, cavitation strip detectors 660 may facilitate monitoring whether lipolysis is proceeding smoothly and substantially uniformly. As the transducer 612 is moved across a patient's skin (not shown) with the intention to destroy a substantially uniform layer of adipose tissue, it may be used to determine when the transducer should be moved to the next position. Preferably, the monitoring system 662 may be coupled to the cavitation strip detectors 660 for correlating cavitation signals detected by the cavitation detectors to facilitate monitoring and/or ensuring a more even rupturing of cells within a layer of fatty tissue. Such a monitoring system 662 may facilitate more uniform cell destruction and may help deliver adequate energy to a given focal zone, thereby preventing overheating or corollary damage to neighboring tissues. Thus, the cavitation strip detectors 660 may provide real-time control and feedback for producing a more uniform removal of the adipose layer.

Although the exemplary methods described herein include lypolysis, i.e., rupturing, destroying, and/or removing adipose tissue, it will be appreciated that the systems and methods of the present invention may be used for treating a variety of subcutaneous tissues. For example, the systems and methods of the present invention may be used to destroy tumors within subcutaneous tissue, such as cancerous tumors, without invasive surgery. Chemotherapy agents may be introduced into a target tissue region before the systems are used to cause cavitation within the tissue region. The ultrasonic cavitation pulse and/or mechanical vibration may cause the membranes of cells within the tissue region to become porous, even if the cells are not totally destroyed. This may enhance the effectiveness of the chemotherapy agents on the cells within the tissue region, as will be appreciated by those skilled in the art.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

What is claimed is:

1. A system for destroying tissue within a subcutaneous tissue region, comprising;
   a transducer device comprising an emission surface for emitting acoustic energy and defining a longitudinal axis, the transducer device configured for focusing the acoustic energy at a substantially linear focal zone that extends substantially parallel to the longitudinal axis in the subcutaneous tissue region;
   drive circuitry coupled the transducer device for providing drive signals to the transducer device whereby the transducer device may emit acoustic energy from the emission surface; and
   a controller coupled to the drive circuitry, the controller configured for controlling the drive signals delivered by the drive circuitry such that the acoustic energy emitted by the transducer device has sufficient intensity to cause mechanical damage and rupture cells within the focal zone, the controller configured for controlling the drive circuitry such that the transducer generates pulses having a duration of between approximately 0.25 and 20 microseconds and has a duty cycle of about twenty percent (20%) or less to minimize heating within the focal zone.

2. The system of claim 1, wherein the drive circuitry is configured for providing drive signals having a frequency ranging from approximately 0.25 MHz to 30 MHz.

3. The system of claim 1, wherein the controller is configured for controlling the drive circuitry such that the transducer has a duty cycle of about one percent or less.

4. The system of claim 1, wherein the transducer device has a partial cylindrical emission surface extending substantially parallel to the longitudinal axis of the transducer.

5. The system of claim 4, wherein the transducer device comprises a substantially planar transducer element and a partial cylindrical lens defining the emission surface, the lens acoustically coupled to the planar transducer element for focusing the acoustic energy at the substantially linear focal zone.

6. The system of claim 4, wherein the emission surface is concave and has a predetermined radius of curvature for focusing the acoustic energy at a predetermined focal distance from the emission surface to the focal zone.

7. The system of claim 4, wherein the transducer device comprises one or more transducer elements disposed in an elongate arcuate configuration, the emission surface comprising an elongate concave inner surface of the one or more transducer elements.

8. The system of claim 7, wherein:
   the transducer comprises a plurality of linear transducer elements disposed adjacent one another and extending substantially parallel to the longitudinal axis of the transducer;
   the drive circuitry is configured for providing respective drive signals to each of the linear transducer elements; and
   the controller is configured for controlling a phase of the respective drive signals to adjust a focal distance from the emission surface to the focal zone.

9. The system of claim 1, wherein the transducer comprises a plurality of elongate linear transducer elements disposed adjacent one another in a substantially planar configuration.

10. The system of claim 9, wherein the drive circuitry is configured for providing respective drive signals to each of the linear transducer elements, and wherein the controller is configured for controlling a phase of the respective drive signals to adjust a focal distance from the emission surface to the focal zone.

11. The system of claim 1, wherein the transducer device comprises a plurality of transducers disposed adjacent to one another, the transducers configured for generating respective substantially linear focal zones that extend generally parallel to one another and are spaced apart from one another.

12. The system of claim 11, wherein a first of the plurality of transducers has a first focal distance and wherein a second of the plurality of transducers has a second focal distance that is different than the first focal distance.

13. The system of claim 1, further comprising a frame to which the transducer device is mounted, the transducer device being movable along the frame in a direction substantially perpendicular to the longitudinal axis for moving the focal zone to successive tissue regions.

14. A method for destroying cells within a subcutaneous tissue region located beneath a patient's skin comprising:
   disposing a transducer externally adjacent to the patient's skin: and
   driving the transducer with drive signals using a relatively low duty cycle such that the transducer emits acoustic energy, while focusing the acoustic energy from the transducer at a localized focal zone within the tissue region, the acoustic energy having sufficient intensity to rupture cells within the focal zone while substantially minimizing heating of tissue within the focal zone,
   wherein the transducer defines a longitudinal axis, and wherein the focal zone comprises a substantially linear focal zone extending substantially parallel to the longitudinal axis.

15. The method of claim 14, wherein the acoustic energy has sufficient energy to vibrate the cells within the focal zone with sufficient mechanical energy to cause the cells to rupture.

16. The method of claim 14, wherein the acoustic energy has a frequency ranging from approximately 0.25 MHz to 30 MHz.

17. The method of claim 16, wherein the transducer comprises an acoustic emission surface defining a portion of a cylinder for focusing the acoustic energy at the substantially linear focal zone.

18. The method of claim 17, wherein the transducer comprises a plurality of transducer elements disposed substantially parallel to the longitudinal axis, and wherein the step of driving the transducer comprises controlling a phase of the drive signals to adjust a focal distance to the focal zone.

19. The method of claim 17, wherein the transducer comprises a generally planar transducer and an acoustic lens defining the emission surface, and wherein the acoustic energy is focused at the focal zone by directing the acoustic energy through the acoustic lens.

20. The method of claim 17, wherein the transducer comprises an arcuate transducer extending substantially parallel to the longitudinal axis.

21. The method of claim 14, further comprising moving the transducer in a direction substantially perpendicular to the longitudinal axis of the transducer, thereby moving the focal zone to a position substantially parallel to a previous position within the tissue region.

22. The method of claim 21, wherein the transducer is mounted to a frame, the transducer being movable along the frame in a direction substantially perpendicular to the longitudinal axis of the transducer.

23. The method of claim 14, wherein the acoustic energy has sufficient intensity to cavitate the cells within the focal zone.

24. A method for destroying cells within a subcutaneous tissue region located beneath a patient's skin, comprising:

disposing a transducer externally adjacent to the patient's skin;

driving the transducer with drive signals using a relatively low duty cycle such that the transducer emits acoustic energy, while focusing the acoustic energy from the transducer at a localized focal zone within the tissue region, the acoustic energy having sufficient intensity to rupture cells within the focal zone while substantially minimizing heating of tissue within the focal zone, the acoustic energy having sufficient intensity to cavitate the cells within the focal zone; and introducing a fluid into the tissue region, the fluid comprising gas bubbles for enhancing cavitation within the tissue region.

25. A method for destroying cells within a subcutaneous tissue region located beneath a patient's skin comprising:

disposing a transducer externally adjacent to a patient's skin;

driving the transducer with drive signals using a relatively low duty cycle such that the transducer emits acoustic energy, while focusing the acoustic energy from the transducer at a localized focal zone within the tissue region, the acoustic energy having sufficient intensity to rupture cells within the focal zone while substantially minimizing heating of tissue within the focal zone, the acoustic energy having sufficient intensity to cavitate the cells within the focal zone;

monitoring cavitation within the focal zone;

correlating the cavitation within the focal zone with an extent of cell destruction within the focal zone; and automatically moving the transducer along the frame to a new location along the external surface of the patient when a predetermined level of cell destruction within the focal zone is obtained.

26. The method of claim 25, wherein the cavitation is monitored by one or more cavitation detectors.

27. The method of claim 26, wherein the cavitation detectors comprise acoustic sensors that produce signals in response to cavitation within the focal zone, and wherein the signals are compared to a database to correlate the cavitation occurring within the focal zone to the extent of cell destruction.

28. The method of claim 27, wherein a rate of change in amplitude of the signals is correlated with an empirical database to determine when the predetermined level of cell destruction is obtained.

29. A method for destroying cells within a subcutaneous tissue region located beneath a patient's skin, comprising:

disposing a transducer externally adjacent to the patient's skin;

driving the transducer with drive signals using a relatively low duty cycle such that the transducer emits acoustic energy, while focusing the acoustic energy from the transducer at a localized focal zone within the tissue region, the acoustic energy having sufficient intensity to rupture cells within the focal zone while substantially minimizing heating of tissue within the focal zone; and introducing gas bubbles into the subcutaneous tissue region to promote cavitation before driving the driving the transducer with drive signals to rupture cells within the focal zone.

30. The method of claim 29, wherein the introducing step comprises injecting a liquid with the gas bubbles suspended or dissolved therein into the subcutaneous tissue region.

31. A method for destroying cells within a subcutaneous tissue region located beneath a patient's skin, comprising:

disposing a transducer externally adjacent to the patient's skin; and driving the transducer with drive signals using a relatively low duty cycle such that the transducer emits acoustic energy, while focusing the acoustic energy from the transducer at a localized focal zone within the tissue region, the acoustic energy having sufficient intensity to rupture cells within the focal zone while substantially minimizing heating of tissue within the focal zone;

wherein the subcutaneous tissue region comprises adipose tissue, and wherein the ruptured cells comprise adipose cells.

* * * * *